United States Patent [19]

Middleton

[11] 3,976,691

[45] Aug. 24, 1976

[54] DIALKYLAMINOSULFUR TRIFLUORIDES AS FLUORINATING AGENTS

[75] Inventor: William Joseph Middleton, Chadds Ford, Pa.

[73] Assignee: E. I. Du Pont de Nemours and Company, Wilmington, Del.

[22] Filed: Jan. 10, 1975

[21] Appl. No.: 539,981

Related U.S. Application Data

[62] Division of Ser. No. 314,022, Dec. 11, 1972, Pat. No. 3,914,265.

[52] U.S. Cl. .......................... 260/544 F; 260/239.5; 260/397.3; 260/465.7; 260/586 R; 260/590 R; 260/591; 260/614 F; 260/632 R; 260/646; 260/648 F; 260/653; 260/593 H; 260/601 H; 260/651 F; 260/650 F

[51] Int. Cl.² ................. C07C 51/58; C07C 17/16; C07C 17/22; C07B 9/00

[58] Field of Search......... 260/544 F, 586 R, 590 R, 260/591, 653, 239.5, 593 H, 651 F, 650 F, 648 F, 614 F, 601 H

[56] References Cited

UNITED STATES PATENTS

| | | | |
|---|---|---|---|
| 3,705,897 | 12/1972 | Murphy............................ | 260/243 C |
| 3,714,245 | 1/1973 | Beckerbauer................... | 260/544 F |
| 3,752,850 | 8/1973 | Scherer et al. .................. | 260/544 F |
| 3,899,531 | 8/1975 | Siegemumd..................... | 260/544 F |

*Primary Examiner*—Norman Morgenstern
*Attorney, Agent, or Firm*—Anthony P. Mentis

[57] ABSTRACT

Dialkylaminosulfur trifluorides such as diethylaminosulfur trifluoride are useful in replacing hydroxyl group and carbonyl oxygen with fluorine in various organic compounds.

5 Claims, No Drawings

DIALKYLAMINOSULFUR TRIFLUORIDES AS FLUORINATING AGENTS

This is a division, of application Ser. No. 314,022, filed Dec. 11, 1972 now U.S. Pat. No. 3,914,265.

BACKGROUND OF THE INVENTION

1. Field of the Invention

This invention relates to a new process for preparing organic fluorine-containing compounds. More particularly, it relates to a process for replacing a hydroxyl group in organic compounds with a fluorine atom and/or the oxygen atom of organic carbonyl compounds with two fluorine atoms by reaction of the hydroxyl or carbonyl compound with a dialkylaminosulfur trifluoride.

2. Description of Prior Art

Several materials have been used in the past as fluorinating agents. The use of sulfur tetrafluoride is disclosed in U.S. Pat. No. 2,859,245 and 2,983,626. W. C. Smith, Angew. Chem. 74, 742 (1962) presents a review of its use. W. A. Sheppard, J.A.C.S. 82, 4751 (1960); 84, 3058 (1962) describes the use of phenylsulfur trifluoride. "Fluoroamine reagent", $(CH_3)_2$—$NCF_2CFHCl$, has also been used. All of these reagents are not completely satisfactory for one reason or another.

The dialkylaminosulfur trifluorides have been previously reported in the literature but no mention has been made of their use as fluorinating agents. The following are mentioned:

1. G. C. Demitras, R. A. Kent and A. C. MacDiarmid, Chem. Ind. (London), 1964, 1712; and G. C. Demitras and A. G. MacDiarmid, Inorg. Chem., 6, 1903 (1967). These papers describe the preparation of $(CH_3)_2NSF_3$ by the reaction of $SF_4$ with $(CH_3)_2NSi(CH_3)_3$. The $^{19}$F nmr spectrum was described.

2. S. P. Von Halasz and O. Glemser, Chem. Ber., 103, 594, (1970), show the preparation of $(C_2H_5)_2NSF_3$ by reaction of $(C_2H_5)_2NSi(CH_3)_3$ with $SF_4$. This compound reacts with $(CH_3)_3Si$—$N$=$C$=$N$—$Si(CH_3)_3$ to give $NCN$=$SFN(C_2H_5)_2$. No other chemistry is reported.

3. S. P. Von Halasz and O. Glemser, Chem. Ber., 104, 1247 (1971), describe the preparation of $RSF_3$ (R = $Me_2N$, $Et_2N$ and piperidino) by the reaction of R—$Si(CH_3)_3$ with $SF_4$. No fluorination reactions are disclosed.

DESCRIPTION OF THE INVENTION

It has now been found that a compound of the formula

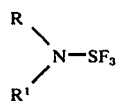

wherein each of R and R[1], alike or different, is a primary alkyl group of up to 4 carbon atoms, or when taken together are —$(CH_2)_4$— or —$(CH_2)_5$—, will react with an organic compound containing hydroxyl and/or carbonyl groups to replace such groups with fluorine. The reaction can be carried out under mild conditions that are often not suitable with known fluorinating agents. For example, the reaction can be run in glass equipment at atmospheric pressure and without the use of an acid catalyst as may be required with $SF_4$.

In general, organic compounds that contain hydroxyl and carbonyl functions will react with dialkylaminosulfur trifluorides to give organic fluorine compounds. These compounds include alcohols, aldehydes, ketones, and carboxylic acids containing up to 40 carbon atoms and which may be monofunctional or polyfunctional. Organic polymeric compositions that contain hydroxyl or carbonyl groups, such as cellulose and vinyl alcohol homopolymers and copolymers, can also be fluorinated with dialkylaminosulfur trifluoride.

The hydroxyl compounds that can be used in this process include monofunctional and polyfunctional aliphatic primary, secondary, and tertiary alcohols and aromatic, heterocyclic, and aliphatic carboxylic acids, all of which may contain other substituents.

The carbonyl compounds that can be used in this process include aliphatic, heterocyclic, and aromatic ketones, aldehydes, and carboxylic acids which may also contain other substituents.

Included also are compounds that contain both hydroxyl and carbonyl functions in the same molecule. In addition to compounds specifically illustrated below by example or structural formula, the following compounds can be used in the process of this invention.

Examples of alcohols that may be used are methanol, ethanol, cyclopentanol, phenylethyl alcohol, isopropanol, tert-butanol, stearyl alcohol, polyvinyl alcohol, glycerin and cholesterol.

Examples of aldehydes that may be used are formaldehyde, acetaldehyde, propionaldehyde, phenylacetaldehyde, phthaladehyde, piperonal, dodecyl aldehyde, n-butyraldehyde, isobutyraldehyde, glyoxal, anthraldehyde, anisaldehyde, acrolein, cinnamaldehyde and crotonaldehyde.

Examples of ketones that may be used are acetone, cyclohexanone, 2-butanone, di-n-hexyl ketone, phorone, pinacolone, and acetonaphthone.

Examples of carboxylic acids that may be used are acetic, succinic, maleic, methacrylic, propionic, acrylic, stearic, glutaric, phenylacetic, and naphthoic acid.

Although esters, amides and phenols are operable in this reaction, they do not work as well as alcohols, aldehydes, ketones and acids.

Generalized equations for the process of this invention are given below, with Q, X and Y representing the radicals of any nature whatsoever attached to the carbon containing the oxygen function to be replaced.

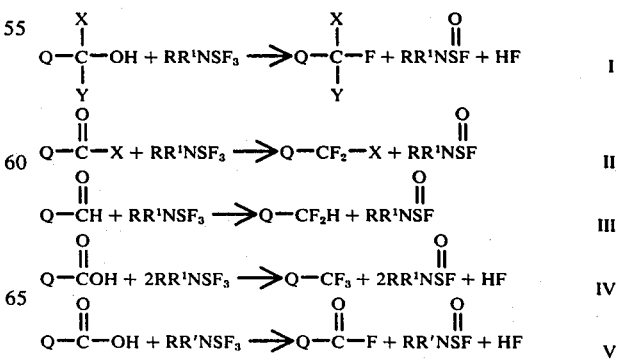

The reaction of the carbonyl or hydroxyl compound with a dialkylaminosulfur trifluoride is conducted under substantially anhydrous conditions. The reaction vessel can be made of metal, glass, plastic or ceramic and can be closed or open to the atmosphere if provisions to exclude moisture are taken.

The reaction is conducted by charging the dialkylaminosulfur trifluoride into the reaction vessel first, and then adding the hydroxyl or carbonyl compound. Alternatively the hydroxyl or carbonyl compound can be charged first, or the hydroxyl or carbonyl compound and the dialkylaminosulfur trifluoride can be charged simultaneously. Solvent is not necessary for the reaction, but the use of a solvent is usually advantageous to moderate the reaction. Either or both of the reactants may be dissolved in an inert solvent before mixing or the reactants may be charged into an inert solvent contained in the reaction vessel.

Solvents suitable for the reaction include hydrocarbons such as benzene, xylene, pentane, hexane, decalin and isooctane; halocarbons such as methylene chloride, ethylene chloride, chloroform, carbon tetrachloride, chlorobenzene, trichlorofluoromethane; ethers such as diethyl ether, dioxane, tetrahydrofuran, ethylene glycol dimethyl ether, and diethylene glycol dimethyl ether; nitriles such as acetonitrile and benzonitrile; nitro compounds such as nitromethane and nitrobenzene; or any solvent inert to both of the reactants.

The reaction is conducted at temperatures from $-100°$ to $+100°$. The preferred range for replacing hydroxyl groups is from $-80°$ to $+35°$, and the preferred range for carbonyl compounds is from $-20°$ to $+80°$. The time of reaction is generally dependent on the temperature and reactivity of the organic oxy or oxo group. Times of an hour or less to a week can be used.

Pressure is not critical. Ambient and/or autogenous pressures are the most convenient and therefore preferred.

The mole ratio of reactants is normally chosen for maximum yield, with one equivalent of dialkylaminosulfur trifluoride needed for each equivalent of hydroxyl or carbonyl present. When more than one hydroxyl or carbonyl group is present in the compound to be fluorinated, the more reactive groups can be selectively reacted by adding the dialkylaminosulfur trifluoride to an excess of the polyfunctional compound, preferably in a solvent to insure good mixing.

The fluorinated products can be separated from the reaction mixture and then purified by any of several standard methods, including distillation, chromatography, solvent extraction, and recrystallization.

The fluorine-containing compounds obtained by this process are gasses, liquids, or solids that have many uses. They can be used as gaseous or liquid carriers in aerosol sprays. They can be used as solvents and thinners in lacquers and paints. They are useful as liquid media for the preparation of dispersions of carbon black and graphite and some are useful as insecticides. They can be used as heat transfer fluids and refrigerants. Most importantly, they can serve as intermediates in the preparation of other fluorine-containing compounds which are otherwise difficult to obtain, including pharmaceuticals, herbicides, insecticides, and other pesticides. The polymeric fluorine-containing products prepared by this process are useful for construction of water and oil resistant objects, such as films and in preparing water and oil resistant coatings.

In general, the dialkylaminosulfur trifluorides can be prepared by the reaction of a dialkylaminotrimethylsilane with sulfur tetrafluoride at a low temperature in an inert solvent. Examples A and B illustrate the preparation of diethylamino- and dimethylaminosulfur trifluoride. The preparation of these, as well as of piperidinosulfur trifluoride, has also been reported by Halarz et al. Chem. Ber. 1971, 104.

Typical preparative procedures are illustrated in Examples A and B.

EXAMPLE A

Diethylaminosulfur Trifluoride

A solution of 96 g (0.66 mole) of diethylaminotrimethylsilane in 100 ml trichlorofluoromethane was added dropwise to a solution of 40 ml (measured at $-78°$, 0.72 mole) of sulfur tetrafluoride in 200 ml of trichlorofluoromethane at $-65°$ to $-60°$. The reaction mixture was warmed to room temperature and then distilled to give 88.86 g (84% yield) of diethylaminosulfur trifluoride as a pale yellow liquid, bp $46°-47°$ (10 mm).

EXAMPLE B

Dimethylaminosulfur Trifluoride

A solution of 40 g (0.34 mole) of dimethylaminotrimethylsilane in 50 ml $CCl_3F$ was added dropwise to a solution of 20 ml (measured at $-78°$, 0.36 mole) of sulfurtetrafluoride in 100 ml $CCl_3F$ at $-65°$ to $-80°$. The reaction mixture was distilled to give 37 g of dimethylaminosulfur trifluoride as a pale yellow liquid, bp $49-49.5°$ (33 mm); $^1H$ nmr $(CCl_3F)$ $\delta$ 3.07 ppm (s).

SPECIFIC EMBODIMENTS OF THE INVENTION

In the illustrative examples below, all parts are by weight unless otherwise stated.

EXAMPLE 1

1-Fluorooctane

A solution of 13.0 g (0.1 mole) of 1-octanol in 25 ml of methylene chloride was added dropwise to a solution of 16.1 g (0.1 mole) of diethylaminosulfur trifluoride in 60 ml methylene chloride cooled to $-70°$ to $-65°$. The reaction mixture was then warmed to 25° and 50 ml of water was added. The lower organic layer was separated, dried ($MgSO_4$) and then distilled to give 12.0 g (90%) of 1-fluorooctane as a colorless liquid: bp $42°-43°$ (20 mm), $^{19}F$ nmr $(CCl_3F)$ $\delta$ $-218.8$ ppm (t, t, 1F, J = 49, 25 Hz).

Anal. Calcd for $C_8H_{17}F$: C, 72.67; H, 12.97; F, 14.37. Found: C, 72.76; H, 13.09; F, 14.44.

EXAMPLE 2

Ethyl 2-Fluoropropionate

A solution of 1.18 g (0.01 mole) of ethyl lactate in 2 ml of methylene chloride was slowly injected into a solution of 1.25 ml (0.01 mole) of diethylaminosulfur trifluoride in 5 ml of methylene chloride cooled to $-78°$. The reaction mixture was then warmed to room temperature and mixed with cold water. The lower layer was separated, washed with water, dried ($MgSO_4$) and distilled to give 0.93 g (78% yield) of ethyl 2-fluoropropionate as a colorless liquid: bp $50°-51°$ (50 mm); $^{19}F$ nmr $(CCl_3F)$ $\delta$ $-184.6$ ppm (d, q, 1F, J = 49, 24 Hz).

Anal. Calcd for $C_5H_9FO_2$: C, 50.00; H, 7.57; F, 15.83. Found: C, 50.11; H, 7.77; F, 16.01.

EXAMPLE 3

2-Fluoro-2-methylbutane

A solution of 11.3 g (0.128 mole) of tert-pentanol in 25 ml of diethyleneglycol dimethyl ether was added dropwise to a solution of 16.1 g (0.1 mole) of diethylaminosulfur trifluoride in 100 ml of diethyleneglycol dimethyl ether cooled to −70°. The most volatile portion of the reaction mixture was distilled out at reduced pressure (1 mm) into a receiver cooled with solid carbon dioxide. The condensate was redistilled to give 7.9 g (88%) of 2-fluoro-2-methylbutane (tert-pentyl fluoride): bp 45°–46°; $^{19}$F nmr (CCl$_3$F) δ −139.2 ppm (m).

Anal. Calcd for C$_5$H$_{11}$F: C, 66.62; H, 12.30; F, 21.08. Found: C, 66.81; H, 12.47; F, 21.72.

EXAMPLE 4

1,1-Difluoro-3-methylbutane

A 1.72-g (0.02 mole) sample of isovaleraldehyde was slowly injected into a stirred solution of 2.5 ml (0.02 mole) of diethylaminosulfur trifluoride in 10 ml of CCl$_3$F at 25°. The reaction mixture was stirred for 30 min., and then mixed with 25 ml of water. The lower organic layer was separated, washed with water, dried (MgSO$_4$) and distilled to give 1.73 g (80%) of 1,1-difluoro-3-methylbutane as a colorless liquid: bp 59°–60°; $^{19}$F nmr (CCl$_3$F) δ −115.5 ppm (d, t, 2F, J = 58, 17 Hz).

Anal. Calcd for C$_5$H$_{10}$F$_2$: C, 55.54; H, 9.33; F, 35.14. Found: C, 55.77; H, 9.61; F, 35.15.

EXAMPLE 5

2-Fluoro-3-butene and 1-Fluoro-2-butene

A solution of 1.44 g (0.02 mole) of 3-butene-2-ol in 2 ml diethyleneglycol dimethyl ether was slowly injected into a stirred solution of 2.5 ml (0.02 mole) of diethylaminosulfur trifluoride in 10 ml of diethyleneglycol dimethyl ether cooled to −78°. The reaction mixture was warmed to 0° and the volatile products were distilled out into a cold trap at reduced pressure to give 1.3 ml of colorless liquid. Gas chromatographic analysis showed the product was a mixture containing 78% 2-fluoro-3-butene and 22% of the isomeric 1-fluoro-2-butene. The product was redistilled to give 1.07 g of colorless liquid: bp 24°–27°; $^{19}$F nmr (CCl$_3$F) δ −171.6 ppm (78% d, q, d, d, J = 46.7, 24. 13.0, 2.7 Hz) and δ −210.0 ppm (22%, t, m, J = 50 Hz).

Anal. Calcd for C$_4$H$_7$F: C, 64.83; H, 9.53; F, 25.64. Found: C, 65.11; H, 9.79; F, 25.37.

This reaction was repeated, except that 2,2,4-trimethylpentane was used as solvent instead of dimethyl ether of diethyleneglycol to give 1.4 ml of a mixture containing 91% 2-fluoro-3-butene and 9% 1-fluoro-2-butene.

EXAMPLE 6

1-Fluoro-2-butene and 2-Fluoro-3-butene

The procedure described for Example 5 was repeated, except that 2-butene-1-ol was used in place of 3-butene-2-ol. When diethyleneglycol dimethyl ether was used as solvent, 1.37 ml of a product containing 72% 2-fluoro-3-butene and 28% 1-fluoro-2-butene was obtained. When 2,2,4-trimethylpentane was used as solvent, 1.5 ml of a product containing 64% 2-fluoro-3-butene and 36% 1-fluoro-2-butene was obtained.

EXAMPLE 7

2-Fluoro-2-methyl-3-butyne

A solution of 1.68 g (0.02 mole) of 2-methyl-3-butyn-2-ol in 2 ml of diethyleneglycol dimethyl ether was added slowly (5 min.) to a stirred solution of 2.5 ml (0.02 mole) of diethylaminosulfur trifluoride in 10 ml of diethyleneglycol dimethyl ether cooled to −78°. The volatile portion of the reaction mixture was distilled out of the reaction mixture under reduced pressure (2 mm) and condensed in a cold trap. Redistillation gave 1.47 g (75%) of 2-fluoro-2-methyl-3-butyne as a colorless liquid: bp 43°–44°; $^{19}$F nmr (CCl$_3$F) δ −129.3 ppm (septet, d, 1F, J = 20, 5 Hz); $^1$H nmr (CCl$_3$F) δ 1.57 ppm (d, 6H, J = 1.5 Hz) and δ 2.58 ppm (d, 1H, J = 5 Hz).

Anal. Calcd for C$_5$H$_7$F: C, 73.44; H, 7.20; F, 19.36. Found: C, 73.68; H, 7.28; F, 19.19.

EXAMPLE 8

3-Fluoro-2,2,3-trimethylbicyclo[2.2.1]heptane

A solution of 3.08 g (0.02 mole) of exo-1,7,7-trimethylbicyclo[2.2.1]heptanol (borneol) in 15 ml of CCl$_3$F was slowly added to a solution of 2.5 ml (0.02 mole) of diethylaminosulfur trifluoride in 10 ml of CCl$_3$F cooled to −78°. The reaction mixture was warmed to room temperature and water was added. The lower layer was separated, washed with water, 5% aqueous NaHCO$_3$ and water again, and then dried (MgSO$_4$). Evaporation to dryness gave 2.87 g of a white solid composed of 20% camphene and 80% 3-fluoro-2,2,3-trimethylbicyclo[2.2.1]heptane. Recrystallization from pentane removed most of the camphene to give 1.97 g of the fluoroheptane as colorless crystals: mp 93°–94°; $^{19}$F nmr (CCl$_3$F) δ −134.4 ppm (q, 1F, J = 24 Hz); $^1$H nmr (CCl$_3$F), absorption due to methyl groups at δ 0.93 ppm (s) and 1.24 ppm (d, J = 24 Hz).

Anal. Calcd for C$_{10}$H$_{17}$F: C, 76.87; H, 10.87; F, 12.16. Found: C, 76.99; H, 11.21; F, 11.97.

The reaction was repeated, using endo-1,7,7-trimethylbicyclo[2.2.1]heptanol instead of the exo isomer to give 1.72 g of the same fluoroheptane, mp 93°–94°.

EXAMPLE 9

1-Fluoro-2-isopropyl-5-methylcyclohexane

A solution of 3.12 g (0.02 mole) of (-)-methanol in 10 ml of CCl$_3$F was slowly injected into a solution of 2.5 ml (0.02 mole) of diethylaminosulfur trifluoride in 10 ml of CCl$_3$F cooled to −78°. The reaction mixture was warmed to room temperature and mixed with water. The organic layer was separated, washed with 5% NaHCO$_3$, dried (MgSO$_4$) nd distilled to give 1.58 g (50%) of 1-fluoro-2-isopropyl-5-methycyclohexane as a colorless liquid: bp 40° (5 mm); $^{19}$F nmr (CCl$_3$F) δ −175.9 ppm (d, J = 50 Hz to m, ½ width Hz).

Anal. Calcd for C$_{10}$H$_{19}$F: F, 12.01. Found: F, 12.12.

EXAMPLE 10

Fluorocyclooctane

A solution of 2.56 g (0.02 mole) of cyclooctanol in 2 ml CCl$_3$F was slowly added to a stirred solution of 2.5 ml (0.02 mole) of diethylaminosulfur trifluoride in 10 ml of CCl$_3$F at −78°. The reaction mixture was warmed to room temperature and water was added. The lower layer was separated, washed with water, 5% NaHCO$_3$, water again, and then dried (MgSO$_4$). The solvent was removed by evaporation at reduced pressure to give 2.5 g of colorless liquid. Analysis by gas chromatography and nuclear magnetic resonance indicated that the product consisted of 70% fluorocyclooctane and 30% cyclooctane.

$^{19}$F nmr (CCl$_3$F) δ −160.5 ppm (d, p, 1F, J = 46, 18 Hz).

$^1$H nmr (for fluorocyclooctane) (CCl$_3$F) δ 4.55 ppm (d, 1H, 46 Hz) and δ 1.2 to 2.4 (m, 14H).

EXAMPLE 11

Benzyl Fluoride

A solution of 2.16 g (0.02 mole) of benzyl alcohol in 5 ml CCl$_3$F was slowly injected into a solution of 2.5 ml (0.02 mole) of diethylaminosulfur trifluoride in 10 ml of CCl$_3$F cooled to −78°. The reaction mixture was warmed to room temperature and then slowly mixed with water. The lower layer was separated, washed with water, dried (MgSO$_4$) and then distilled to give 1.65 g (75%) of benzyl fluoride, bp 139°; $^{19}$F nmr (CCl$_3$F) δ −207.5 ppm (t, J = 49 Hz).

EXAMPLE 12

Benzyl Fluoride

A solution of 0.90 ml (0.01 mole) of dimethylaminosulfur trifluoride in 5 ml methylene chloride was cooled to −78°, and a solution of 1.08 g (0.01 mole) of benzyl alcohol in 2 ml methylene chloride was slowly injected. The reaction mixture was warmed to room temperature and mixed with water. The lower layer was separated, dried (MgSO$_4$) and analyzed by gas chromatography and $^{19}$F nmr. The analyses showed that benzyl fluoride was formed in near-quantitative yield.

EXAMPLE 13

4,4-Difluorohexane

A solution of 16.1 g (0.1 mole) diethylaminosulfur trifluoride in 10 ml CCl$_3$F was added dropwise to a solution of 11.4 g (0.1 mole) of 4-heptanone in 25 ml CCl$_3$F. Water, 5 μl, was added as a catalyst, and the reaction mixture was stirred at room-temperature for one week. Distillation gave 9.2 g (68%) of 4,4-difluoroheptane, bp 90°–110°, contaminated with a small amount of an immiscible liquid. The distillate was washed with water, dried (MgSO$_4$) and redistilled to give 7.1 g of pure product: bp 110°–111°; n$_D^{25}$ 1.3644; $^{19}$F nmr (CCl$_3$F) −98.6 ppm (p, 2F, J = 15 Hz); $^1$H nmr (CCl$_3$F) δ 0.95 ppm (m, 6H), 1.55 ppm (m, 8H).

Anal. Calcd for C$_7$H$_{14}$F$_2$: C, 61.74; H, 10.36; F, 27.90. Found: C, 62.13; H, 10.16; F, 28.07.

EXAMPLE 14

1,1-Difluoroethylbenzene

A solution of 2.5 ml (0.02 mole) of diethylaminosulfur trifluoride and 2.4 g (0.02 mole) of acetophenone in 12 ml of ethyleneglycol dimethyl ether was heated to reflux for 20 hr and then cooled and mixed with water. The reaction mixture was extracted with CCl$_3$F, and the extract was dried (MgSO$_4$) and distilled to give 0.8 g of recovered acetophenone, bp 108°–112° (40 mm), and 1.2 g (66% yield, 42% conversion) of 1,1-difluoroethylbenzene: bp 64°–65° (40 mm); $^{19}$F nmr (CCl$_3$F) δ −87.7 ppm (q, J = 18 Hz).

Anal. Calcd for C$_8$H$_8$F$_2$: C, 67.60; H, 5.67; F, 26.73. Found: C, 67.72; H, 5.73; F, 26.83.

EXAMPLE 15

3,3,7,7-Tetrafluoro-1,5-dimethylbicyclo[3.3.0]octane and 3,3-Difluoro-1,5-dimethylbicyclo[3.3.0]octan-7-one A solution of 8.3 g (0.05 mole) of 1,5-dimethylbicyclo[3.3.0]octane-3,7-dione and 17.7 g (0.11 mole) of diethylaminosulfur trifluoride in 50 ml of benzene was heated at reflux for 24 hr and then cooled and poured into 100 ml of water. The organic layer was separated, dried (MgSO$_4$), and the benzene was distilled off. The residue was sublimed at 150° (1 mm) to give 6.3 g of 80:20 mixture of 3,3,7,7-tetrafluoro-1,5-dimethylbicyclo[3.3.0]octane and 3,3-difluoro-1,5-dimethylbicyclo[3.3.0]octan-7-one.

The mixture was separated by liquid chromatography on an Al$_2$O$_3$ column using pentane and ether. The tetrafluoride (3.7 g) was obtained as white, waxy crystals with a camphorlike odor: mp 16°–109°; $^{19}$F nmr (CCl$_3$F) δ −86.2 ppm (J$_{HF}$ = 14 Hz) and −86.6 ppm (J$_{HF}$ = 14 Hz).

Anal. Calcd for C$_{10}$H$_{14}$F$_4$: C, 57.14; H, 6.71; F, 36.15. Found: C, 57.12; H, 6.82; F, 36.14.

The difluoride (0.8 g) was obtained as light yellow crystals: mp 145°–150°; $^{19}$F nmr (CCl$_3$F) δ −80.9 and −81.0 ppm (J$_{FH}$ = 14 Hz); ir (KBr) 5.72 μ (C═O).

Anal. Calcd for C$_{10}$H$_{14}$F$_2$O: C, 63.81; H, 7.50; F, 20.19. Found: C, 63.07; H, 7.31; F, 20.87.

EXAMPLE 16

Benzal Fluoride

A 25-ml (0.2 mole) sample of diethylaminosulfur trifluoride was added dropwise over a period of 30 min. to a stirred solution of 21.2 g (0.2 mole) of benzaldehyde in 75 ml of methylene chloride at 25°. The reaction mixture was cooled to keep the temperature below 35°. Stirring was continued for 2 hr, and then 100 ml of water was added. The lower layer was separated, washed with 5% NaHCO$_3$ solution and then water, and dried (K$_2$CO$_3$). Distillation gave 19.2 g (75%) of benzal fluoride; bp 57° (35 mm); $^{19}$F nmr (CCL$_3$F) δ −110.9 ppm (d, J = 57.5 Hz).

EXAMPLE 17

Benzoyl Fluoride

Diethylaminosulfur trifluoride, 2.5 ml (0.02 mole) was slowly added to a stirred solution of 2.44 g (0.02 mole) of benzoic acid in 20 ml methylene chloride cooled to 0°. Powdered sodium fluoride, 1 g, was added to remove the HF, and the reaction mixture was filtered. The filtrate was distilled to give 1.98 g (80%) of benzoyl fluoride as a colorless liquid, bp 50° (10 mm) (identified by its infrared spectrum).

EXAMPLE 18

Benzotrifluoride

Diethylaminosulfur trifluoride, 8.05 g (0.05 mole) was added dropwise to a solution of 2.44 g (0.02 mole) of benzoic acid in 20 ml of diethyleneglycol dimethyl ether cooled to 0°. Sodium fluoride (1 g) was then added to remove the HF, and the reaction mixture was warmed to 80° for 20 hr. The most volatile products were distilled from the reaction mixture and then redistilled to give 1.46 g (50%) of benzotrifluoride, bp 102°–103°; $^{19}$F nmr (CCl$_3$F).

EXAMPLE 19

Preparation of Benzhydryl 3-Fluoromethyl-7-(2-thienylacetamido)-3-cephem-4-carboxylate-1-oxide

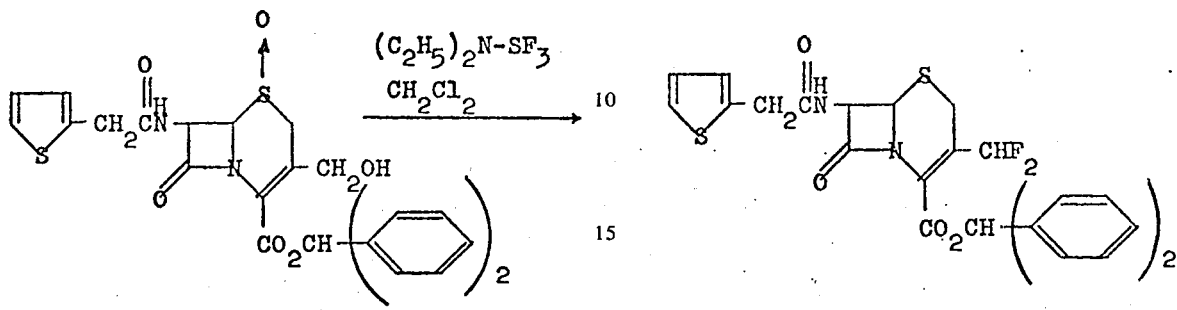

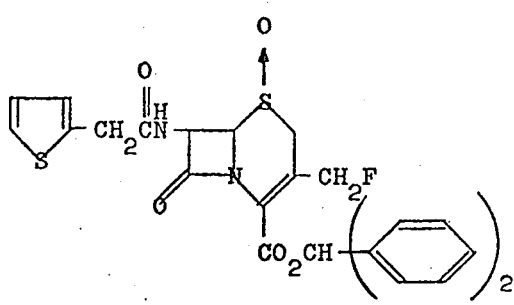

To a solution of 0.483 g (3.0 mmoles) of diethylaminosulfur trifluoride in 10 ml of CH$_2$Cl$_2$ at −78° under N$_2$ was added a solution of 1.61 g (3.0 mmoles) of benzhydryl 3-hydroxymethyl-7-(2-thienylacetamido)-3-cephem-4-carboxylate-1-oxide in 50 ml of CH$_2$Cl$_2$ and the mixture was stirred at −78° for 0.5 hr, then poured into 100 ml of water. The CH$_2$Cl$_2$ layer was dried (MgSO$_4$) and evaporated in vacuo. The residue was chromatographed on silica gel with 9:1 CH$_2$Cl$_2$-acetone to yield 0.095 g of benzhydryl 3-fluoromethyl-7-(2-thienylacetamido)-3-cephem-4-carboxylate-1-oxide in fractions 12–15, rf = 0.60 on tlc with 9:1 CH$_2$Cl$_2$-acetone; mp 205.5°–207.5° d; ir (CHCl$_3$) 3450 (amide N—H), 1805 (β-lactam C=O), 1725 (ester C=O), 1680 (amide C=O), 1495 ("amide II" band), and 700 (aromatic) cm$^{-1}$.

Anal. Calcd for C$_{27}$H$_{23}$N$_2$O$_5$S$_2$F: C, 60.22; H, 4.28; N, 5.20; F, 3.54. Found: C, 59.40; H, 4.29; N, 5.20; F, 3.60.

EXAMPLE 20

Preparation of Benzhydryl 3-Difluoromethyl-7-(2-thienylacetamido)-3-cephem-4-carboxylate

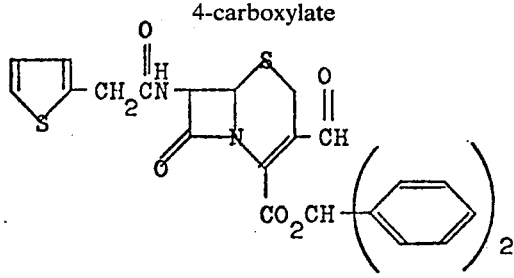

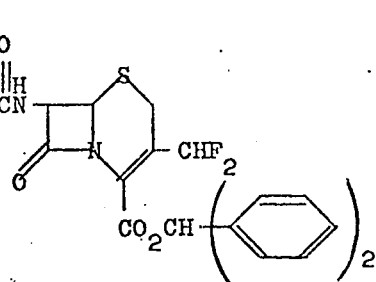

A solution of 0.518 g of benzhydryl 3-formyl-7-(2-thienylacetamido)-3-cephem-4-carboxylate and 1.0 ml of diethylaminosulfur trifluoride in 25 ml CH$_2$Cl$_2$ was stirred at 27° for 2.0 hr and then poured into 25 ml of water. The CH$_2$Cl$_2$ phase was dried (MgSO$_4$) and stripped in vacuo. The residue was chromatographed on silica with CHCl$_3$ to yield 0.264 g (49%) of a 1:1 mixture of Δ$^3$:Δ$^2$ benzhydryl 3-difluromethyl-7-(2-thienylacetamido)-cephem-4-carboxylates; ir (CHCl$_3$) 3450 (amide N-H), 1820 (β-lactam C=O), 1750 (ester C=O), 1695 (amide C=O), and 1510 ("amide II" band) cm$^{-1}$; $^{19}$F nmr (CHCl$_3$) δ 116.43 (d (J$_{HF}$ = 57 Hz), —CHF$_2$ (one of Δ$^2$+Δ$^3$ isomers)) and and 115.82 (d (J$_{HF}$ = 57 Hz), —CHF$_2$ (other isomer)); $^1$H nmr (CDCl$_3$) δ 3.5 (2, m, C$_2$—CH$_2$ (Δ$^3$-isomer)), 3.74 (2, s, thienyl —CH$_2$), 4.94 (1, d (J = 6 Hz), C$_6$-H), 5.91 (1, dd (J = 6 Hz, J$^1$ = 10 Hz), C$_7$-H), 6.72 (1, t (J$_{HF}$ = 57 Hz), —CHF$_2$), and 7.3 (13, m, aryl + thiophene —H); uv max (C$_2$H$_5$OH) 265 nm (7400).

Anal. Calcd for C$_{27}$H$_{22}$N$_2$O$_4$S$_2$F$_2$: C, 59.99; H, 4.10; N, 5.18. Found: C, 59.82; H, 3.94; N, 5.01.

EXAMPLE 21

1,4-Diisopropyl-2-benzoyl Fluoride

To 4.12 g (0.02 mole) 1,4diisopropyl-2-benzoic acid in 25 ml cold benzene was added dropwise through a syringe 2.5 ml (0.02 mole) diethylaminosulfur trifluoride. The exothermic reaction was controlled by an ice bath. The solution was poured into water and extracted with benzene. The benzene was evaporated off yielding 3.94 g (96% yield) of the acid fluoride.

Anal: ir consistent with an authentic sample.

EXAMPLE 22

1,2-Difluoroethane

A solution of 620 mg (0.01 mole) of ethylene glycol in 2 ml of diethyleneglycol dimethyl ether was slowly added to a stirred solution of 2.5 ml (0.02 mole) of diethylaminosulfur trifluoride in 10 ml of diethyleneglycol dimethyl ether cooled to −78°. The reaction mixture was warmed to room temperature and the most volatile components were distilled out under reduced pressure into a cold trap. Redistillation gave 0.35 ml of 1,2-difluoroethane as a colorless liquid; bp 25°–27°; $^{19}$F nmr (CCl$_3$F) δ −225.9 ppm (m).

EXAMPLE 23

1-Chloro-2-fluoroethane

EXAMPLE 25

Fluorination of Polyvinylbutyral/Polyvinyl Alcohol

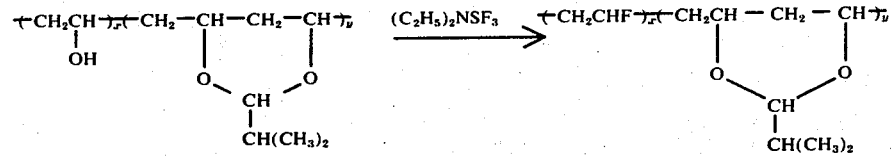

A solution of 1.61 g (0.02 mole) of ethylene chlorohydrin in 2 ml diethyleneglycol dimethyl ether was slowly added to a solution of 2.5 ml (0.02 mole) diethylaminosulfur trifluoride in 10 ml of diethyleneglycol dimethyl ether cooled to −78°. The reaction mixture was warmed to room temperature and the most volatile portion was distilled out under reduced pressure into a cold trap. Redistillation gave 1.11 g (69%) of 1-chloro-2-fluoroethane as a colorless liquid, bp 50°–53°; $^{19}$F nmr (CCl$_3$F) δ −219.8 ppm (t, t, 1F, J = 48, 25 Hz).

EXAMPLE 24

1-(Difluoromethyl)naphthalene

Diethylaminosulfur trifluoride, 25 ml (ca. 0.2 mole) was added dropwise to a stirred solution of 31.24 g (0.20 mole) of 1-naphthaldehyde in 100 ml methylene chloride at 25°. The reaction mixture was stirred for 18 hr, and then mixed with 100 ml of ice-water. The lower organic layer was separated, washed with 5% NaHCO$_3$ solution and then water, and dried (MgSO$_4$). Distillation gave 16.4 g (72% yield, 46% conversion) of 1-(difluoromethyl)naphthalene, bp 78°–79° (0.4 mm) and 11.2 g (36%) of recovered naphthaldehyde. $^{19}$F nmr (CCl$_3$F) δ −111.1 ppm (d, J = 56 Hz). $^1$H nmr (CCl$_3$F) δ 8.3 to 7.1 ppm (m, 7 aromatic H) and δ 6.98 ppm (t, J = 56 Hz).

Anal. Calcd for C$_{11}$H$_8$F$_2$: C, 74.15; H, 4.53; F, 21.32. Found: C, 74.22; H, 4.16; F, 21.18.

Diethylaminosulfur trifluoride, 2.5 ml (0.02 mole), was slowly injected into a stirred solution of 2.1 g of polyvinylbutyral (containing 21 weight % of polymerized polyvinylalcohol in random distribution) in 100 ml of ethyleneglycol dimethyl ether cooled to 0°. The reaction mixture was slowly warmed to room temperature, and the solution was evaporated to dryness under reduced pressure, first at room temperature and then at 60°. There was obtained 2.1 g of rubbery film which had improved oil and water repellent properties over the untreated polyvinylbutyral.

Anal. Found: F, 2.34%.

EXAMPLE 26

Fluorination of Cellulose

A throughly dried Soxhlet thimble, 33 mm in diameter and 94 mm long (3.90 g), made of highly purified cellulose, was suspended in a solution of 2.5 ml diethylaminosulfur trifluoride in 250 ml methylene chloride at 25° for 24 hr. The thimble was removed, washed with methylene chloride, and dried in vacuum. The treated thimble was water-repellent, as shown by the fact that it held liquid water for at least 5 hr before any seepage occurred. An untreated thimble allowed water to pass through rapidly. Analysis indicated that the treated thimble contained 0.69% fluorine.

Equations for additional reactions that can be accomplished by using this process are illustrated below.

| Hydroxyl or Carbonyl Cpd. | Dialkylaminosulfur Trifluoride | Product |
|---|---|---|
| HOCH$_2$CH$_2$O—CH$_2$CH$_2$CN | ⟨N—SF$_3$⟩ (pyrrolidine) | FCH$_2$CH$_2$OCH$_2$CH$_2$CN |
| (CH$_3$)$_2$NCO—CH$_2$CH$_2$OH (O) | C$_2$H$_5$\N—SF$_3$ / CH$_3$ | (CH$_3$)$_2$NCOCH$_2$CH$_2$F (O) |
| BrCH$_2$CH$_2$OH | (n—C$_4$H$_9$)$_2$NSF$_3$ | BrCH$_2$CH$_2$F |
| HOCH$_2$CH (O) | ⟨N—SF$_3$⟩ (piperidine)  1 equivalent | FCH$_2$CH (O) |
| CH$_3$OCH$_2$COH (O) | (C$_2$H$_5$)$_2$NSF$_3$  1 equivalent | CH$_3$OCH$_2$CF (O) |
| CH$_3$OCH$_2$COH (O) | (CH$_3$)$_2$NSF$_3$  2 equivalents | CH$_3$OCH$_2$CF$_3$ |
| ⟨⟩—⟨⟩—CH$_2$COCH$_2$CH$_2$OH (O) | (C$_2$H$_5$)$_2$NSF$_3$ | ⟨⟩—⟨⟩—CH$_2$COCH$_2$CH$_2$F (O) |

-continued

| Hydroxyl or Carbonyl Cpd. | Dialkylaminosulfur Trifluoride | Product |
|---|---|---|
| Ar-N(CH₃)—COCH₂OH | $(CH_3)_2NSF_3$ | Ar-N(CH₃)—COCH₂F |
| $HO(CH_2)_4OH$ | $(C_2H_5)_2NSF_3$ 2 equivalents | $F(CH_2)_4F$ |
| $HO(CH_2)_4OH$ | $(CH_3)_2NSF_3$ 1 equivalent | $F(CH_2)_4OH$ |
| $HOCH_2CCH_2OH$ (with C=O) | $(CH_3)_2NSF_3$ 2 equivalents | $FCH_2CCH_2F$ (with C=O) |
| $(HOCH_2CH_2)_2S$ | $(CH_3)_2NSF_3$ 2 equivalents | $(FCH_2CH_2)_2S$ |
| $HOCH_2CH_2NO_2$ | $(CH_3)_2NSF_3$ | $FCH_2CH_2NO_2$ |
| steroid with COCH₃ and 3-HO | $(C_2H_5)_2NSF_3$ | steroid with COCH₃ and 3-F |
| steroid with 17-keto and 3-HO | $(CH_3)_2NSF_3$ | steroid with 17-keto and 3-F |

I claim:

1. A process for producing a fluorinated compound comprising contacting a compound of the formula

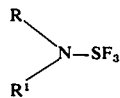

wherein each of R and R¹, alike or different, is a primary alkyl group of up to 4 carbon atoms or when taken together are —(CH₂)₄— or —(CH₂)₅— with a monomeric reactant selected from the group consisting of an aldehyde, ketone and carboxylic acid, under substantially anhydrous conditions at a temperature range of −100° to +100°C.

2. The process of claim 1 carried out at −20° to +80°C.

3. The process of claim 1 wherein the said reactant is an aldehyde.

4. The process of claim 1 wherein the said reactant is a carboxylic acid.

5. The process of claim 1 wherein the said reactant is a ketone.

* * * * *